(12) United States Patent
Branlard et al.

(10) Patent No.: US 6,509,023 B1
(45) Date of Patent: Jan. 21, 2003

(54) COSMETIC COMPOSITION COMPRISING A FUNCTIONALIZED POLYORGANOSILOXANE

(75) Inventors: Paul Branlard, Lyons (FR); Gérard Mignani, Lyons (FR); Claudie Willemin, Paris (FR); Philippe Olier, Lyons (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/463,677

(22) PCT Filed: Jul. 30, 1998

(86) PCT No.: PCT/FR98/01700

§ 371 (c)(1),
(2), (4) Date: Apr. 13, 2000

(87) PCT Pub. No.: WO99/06018

PCT Pub. Date: Feb. 11, 1999

(30) Foreign Application Priority Data

Jul. 31, 1997 (FR) .............................................. 97 09811
Apr. 9, 1998 (FR) ............................................. 98 04483

(51) Int. Cl.$^7$ ................................................... A61K 7/00
(52) U.S. Cl. ....................................................... 424/401
(58) Field of Search ......................................... 424/401

(56) References Cited

U.S. PATENT DOCUMENTS 5,455,026 A * 10/1995 Bahr et al. ..................... 424/65

FOREIGN PATENT DOCUMENTS

WO    WO-94/08557    *  4/1994

* cited by examiner

Primary Examiner—Jose'G. Dees
Assistant Examiner—Konata M. George

(57) ABSTRACT

The invention concerns a cosmetic composition comprising a specific functionalized organopolysiloxane which is linear or cyclic. Said functionalized organopolysiloxane is used as emollient and/or carrier and/or anti-transfer agent in cosmetic compositions.

1 Claim, No Drawings

COSMETIC COMPOSITION COMPRISING A FUNCTIONALIZED POLYORGANOSILOXANE

This application is an application under 35 U.S.C. Section 371 of International Application Number PCT/FR98/01700, filed on Jul, 30, 1998.

The present invention relates to a cosmetic composition comprising at least one functionalized polyorganosiloxane, as well as to the use of the said polyorganosiloxane as an emollient and/or vehicle and/or a transfer-resistance agent in cosmetic compositions for the skin and/or the hair.

A first subject of the invention consists of a cosmetic composition comprising at least one linear functionalized polyorganosiloxane of formula (I)

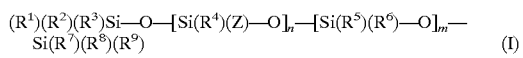
$$(R^1)(R^2)(R^3)Si\text{—}O\text{—}[Si(R^4)(Z)\text{—}O]_n\text{—}[Si(R^5)(R^6)\text{—}O]_m\text{—}Si(R^7)(R^8)(R^9) \quad (I)$$

or a cyclic functionalized polyorganosiloxane of formula (I')

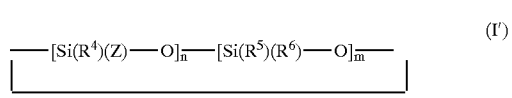
$$\text{—}[Si(R^4)(Z)\text{—}O]_{\overline{n}}\text{—}[Si(R^5)(R^6)\text{—}O]_{\overline{m}}\text{—} \quad (I')$$

in which:

in formula (I)
- n is an integer or decimal number which can range from 0 to 5, preferably equal to 0 or 1, at least one of the radicals $R^1$ and $R^9$ representing the symbol Z when n is equal to 0
- m is an integer or decimal number which can range from 0 to 5, preferably equal to 0 in formula (I')
- n is an integer or decimal number which can range from 1 to 5, preferably equal to 1
- m is an integer or decimal number which can range from 1 to 5, with n+m at least equal to 3 in formulae (I) and (I')
- the symbols $R^1$ and $R^9$ are identical or different and represent the symbol Z or an alkyl radical containing from 1 to 8 carbon atoms, preferably 1 or 2 carbon atoms, most particularly 1 carbon atom
- the symbols $R^2$, $R^3$, $R^4$, $R^5$, $R^6$, $R^7$ and $R^8$ are identical or different and represent an alkyl radical containing from 1 to 8 carbon atoms, preferably 1 or 2 carbon atoms, most particularly 1 carbon atom
- the symbol Z represents,
    - a linear or branched, saturated or unsaturated, $C_6$–$C_{20}$ haloaliphatic radical, in particular a chloro- or fluoroaliphatic radical
    - a radical —X—Y, in which X represents a saturated or unsaturated, linear or branched aliphatic multivalent group containing from 2 to 10 carbon atoms, and Y represents
        - an aryl radical, preferably a $C_6$ aryl radical, optionally substituted with at least one $C_1$–$C_8$ alkyl or $C_6$ aryl group or a halogen atom (in particular chlorine or fluorine),
        - an ethylenically unsaturated $C_5$–$C_6$ cycloaliphatic radical optionally substituted with at least one $C_1$–$C_8$ alkyl group or a halogen atom (in particular chlorine or fluorine),
        - a saturated $C_5$–$C_6$ cycloaliphatic radical substituted with at least one halogen atom (in particular chlorine or fluorine),
        - $C_4$–$C_9$ hydrocarbon-based heterocyclic radical containing at least one nitrogen and/or oxygen and/or sulphur hetero atom, the radical optionally being substituted with at least one $C_1$–$C_8$ alkyl or $C_6$ aryl group or a halogen atom (in particular chlorine or fluorine),
    - the said symbol Z also possibly representing a phenyl radical (directly linked to the silicon) when n+m is equal to 0.

The said functionalized polyorganosiloxanes of formula (I) or (I') have the following Hansen solubility space parameters $\delta_D$ of London interactions ranging from 8 to 21 $(J/cm^3)^{1/2}$ $\delta_P$ of Keesom interactions of greater than 0 and possibly ranging up to 25 $(J/cm^3)^{1/2}$ $\delta_H$ of hydrogen bonding ranging from 0 to 23 $(J/cm^3)^{1/2}$.

The three-dimensional solubility space, in which the solvents and all the organic molecules exist, is defined by C M Hansen in "The three dimensional solubility parameters" J. Paint Technol. 39, 105 (1967); $\delta_D$, $\delta_P$ and $\delta_H$ represent the partial solubility parameters associated, respectively, with the London dispersion forces, the Keesom polarity forces and the hydrogen bonding forces, given that these partial parameters are the components of the overall solubility parameter $\delta$, referred to as the Hildebrand solubility parameter, associated with the voluminal cohesion of the molecule.

The said multivalent group X connecting the radical Y to the silicon can preferably be a divalent alkanediyl or alkenediyl group containing two carbon atoms, ethylene, methylmethylene or ethenylene, or three carbon atoms, methylethylene or methylethenylene.

As examples of radicals Z, mention may be made more particularly of the radicals obtained by opening the vinylic double bond of styrene, of α-methylstyrene, of α-methylstyrene dimer, of limonene, of vinylpyrrolidone, etc., or the terminal triple bond of phenylacetylene, etc.

The said radical Z is preferably a phenyl radical, a phenylalkyl radical in which the alkyl residue contains from 2 to 10 carbon atoms, or a phenylalkenyl radical in which the alkenyl residue contains from 2 to 10 carbon atoms, in particular phenyl(methyl)methyl, phenylethenyl and, most particularly, phenylethyl. Most preferably, the cosmetic composition comprises a mixture of polyorganosiloxanes predominantly containing a polyorganosiloxane containing a phenylethyl radical, a smaller amount of a polyorganosiloxane containing a phenyl(methyl)methyl radical and a small amount of a polyorganosiloxane containing a phenylethenyl radical.

Preferably, the said polyorganosiloxane is a diorganosiloxane MM of formula (I) in which n and m are equal to 0 and Z is a phenyl radical, in particular diphenyltetramethyldisiloxane, or a linear organotrisiloxane MDM of formula (I) in which n is equal to 1 and m is equal to 0, the symbols $R^1$, $R^2$, $R^3$, $R^4$, $R^7$, $R^8$ and $R^9$ preferably being methyl radicals.

Most particularly, the invention is directed towards a cosmetic composition comprising at least one organotrisiloxane containing a phenylalkyl or phenylalkenyl function, of formula (III)

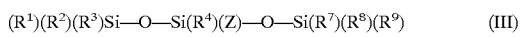
$$(R^1)(R^2)(R^3)Si\text{—}O\text{—}Si(R^4)(Z)\text{—}O\text{—}Si(R^7)(R^8)(R^9) \quad (III)$$

in which formula
- the symbols $R^1$, $R^2$, $R^3$, $R^4$, $R^7$, $R^8$ and $R^9$ are identical or different and represent an alkyl radical containing from 1 to 8 carbon atoms, preferably 1 or 2 carbon atoms, most particularly 1 carbon atom the symbol Z represents a phenyl radical linked to the silicone via a linear or branched divalent alkanediyl or alkenediyl group containing 2 or 3 carbon atoms, preferably 2 carbon atoms.

Examples of functionalized polyorganosiloxanes that are most particularly advantageous according to the invention are organotrisiloxanes containing a phenylalkyl or phenylalkenyl function, of formulae (a) to (e) below Me$_3$SiO—(Me)Si(CH$_2$—CH$_2$—Ph)O—SiMe$_3$     (a)

Me$_3$SiO—(Me)Si[CH(Me)—Ph]O—SiMe$_3$     (b)

Me$_3$SiO—(Me)Si(CH=CH—Ph)O—SiMe$_3$     (c)

Me$_3$SiO—(Me)Si(CH$_2$—CH(Me)—Ph)O—SiMe$_3$     (d)

Me$_3$SiO—(Me)Si[CH=C(Me)—Ph]O—SiMe$_3$     (e)

and diphenyltetramethyldisiloxane of formula PhSi(Me)$_2$Ph

The said polyorganosiloxanes of formula (I) or (I') in which the radical (Z) is other than phenyl can be obtained in a known manner by hydrosilylation between at least one hydrogeno polyorganosiloxane of formula (II) or (II')

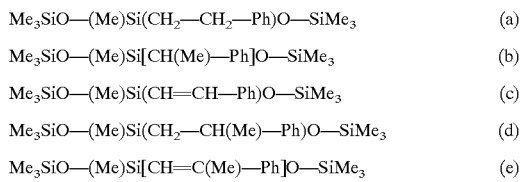

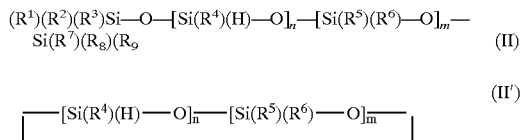

in which formulae R$^1$, R$^2$, R$^3$, R$^4$, R$^5$, R$^6$, R$^7$, R$^8$, R$^9$, n and m have the same meaning as those given above, and the compound containing vinylic or terminal acetylenic unsaturation from which the radical Z is derived, in the presence of a hydrosilylation catalyst, in particular such as platinum.

This operation can be carried out with a slight excess of one or other of the reagents, generally up to 10 mol % relative to the stoichiometry, at a temperature of from about 50° C. to 100° C., preferably from about 50° C. to 80° C., in the presence of 5 to 50 parts by mass of platinum (for example Karstedt catalyst) per million parts by mass of monomers used.

The hydrogenopolyorganosiloxanes preferably used are hydrogenoheptaorganotrisiloxanes MD'M, particularly hydrogenoheptamethyltrisiloxane.

Among the compounds containing vinylic or terminal acetylenic unsaturation which can be used, mention may be made of styrene, α-methylstyrene, α-methylstyrene dimer, limonene, vinylpyrrolidone and acetylene. The said compound is preferably styrene.

One specific embodiment of the first subject of the invention consists of a cosmetic composition comprising phenylmethylheptamethyltrisiloxane of formula Me$_3$Si—O—Si(Me)(Z$^1$)—O—SiMe$_3$, in which Z$^1$ represents the —CH$_2$—CH$_2$—Ph function or a mixture (M) of functionalized heptamethyltrisiloxanes consisting for more than 70% by mass, generally for at least 75% by mass, of trisiloxane of formula Me$_3$Si—O—Si(Me)(Z$^1$)—O—SiMe$_3$, in which Z$^1$ represents the —CH$_2$—CH$_2$—Ph function for less than 25% by mass, generally from 10 to 20% by mass, of trisiloxane of formula Me$_3$Si—O—Si(Me)(Z$^2$)—O—SiMe$_3$, in which Z$^2$ represents the —CH(CH$_3$)—Ph function and less than 5% by mass, generally from 0 to 2% by mass, of trisiloxane of formula Me$_3$Si—O—Si(Me)(Z$^3$)—O—SiMe$_3$, in which Z$^3$ represents the —CH=CH—Ph function in which formulae Me represents a methyl radical and Ph represents a phenyl radical.

The said mixture (M) can be obtained by hydrosilylation reaction at a temperature of from 50 to 150° C., preferably from 50 to 100° C., most particularly from 60 to 90° C., of hydrogenoheptamethyltrisiloxane (reagent SiH) and of styrene (reagent Vi), in the presence of hexamethyldisiloxane as solvent. This hydrosilylation operation is carried out by simultaneously introducing the two reagents (Vi) and (SiH) into the reaction medium comprising the solvent and a hydrosilylation catalyst, this introduction being carried out such that the respective amounts of the two reagents (Vi) and (SiH) correspond to a reagent (Vi)/reagent (SiH) molar ratio of from more than 0.5 to 1.5, preferably of from more than 1 to 1.2, and that, at any moment in the hydrosilylation reaction, the amount of reagent (SiH) present, expressed as mass of (SiH) functions (29 g per 1 function) corresponds to less than 2%, preferably less than 1% of the reaction mass, excluding the mass of solvent.

In the definition of a mole of hydrogenoheptamethyltrisiloxane, reagent (SiH), the —SiH function is considered as being the elemental species. In the definition of a mole of styrene, reagent (Vi), a gram-molecule of styrene is considered as the elemental species.

Karstedt hydrosilylation catalyst is used, for example, in a proportion of from 1 to 300 parts, preferably from 5 to 100 parts, by mass of platinum per million parts per mass of reagents (SiH) and (Vi) used.

The hydrosilylation operation is preferably carried out under atmospheric pressure. The introduction of the reagents (SiH) and (Vi) is preferably carried out by simultaneously adding the two reagents continuously to the reaction mass comprising the solvent and the catalyst. The duration of the additions is adjusted such that the reagent (Vi) is consumed by hydrosilylation as it is introduced.

The solvent and the unreacted reagents are then removed. Their removal can be carried out by distillation under vacuum or under reduced pressure (for example from about 1.013 Pa to 101,300 Pa).

This distillation operation is followed by a hydrogenation operation. This can be carried out at a temperature from about 25 to 200° C., preferably from about 50 to 150° C., at a hydrogen pressure from about 0 to 50 bar, preferably from about 5 to 25 bar, in the presence of a hydrogenation catalyst such as platinum or palladium, in an amount of from 0.01 to 5%, preferably from 0.01 to 1%, by weight of metal relative to the mass to be hydrogenated.

The medium is then optionally subjected to an operation to remove the products other than the heptamethyltrisiloxanes containing polarizable functions. This removal operation can be carried out by distillation under vacuum or under reduced pressure, for example from about 1.013 Pa to 101,300 Pa.

The terms "cosmetic composition" and "cosmetic formulation" mean any cosmetic product or preparation of the type described in Annex I ("Illustrative list by category of cosmetic products") of European Directive No. 76/768/EEC of Jul. 27, 1976, known as the Cosmetics Directive.

The cosmetic compositions can be formulated in a large number of types of product for the skin and/or the hair such as mousses, gels (in particular styling gels), masks for the face or the hair, conditioners, formulations for improving hairstyling, or for facilitating the combing or disentangling of the hair, for providing volume or sheen, rinsing formulations, hand and body lotions and oils, products for improving the moisturization of the skin, cleansing milks, make-up-removing compositions, creams or lotions for protecting against the sun and ultraviolet radiation, care and/or treatment milks and creams, anti-acne preparations, local analgesics, mascaras, products intended to be applied to the lips or other mucuous membranes, sticks, deodorant and antiperspirant products, shaving lotions, bath oils, talcs and other compositions of the same type.

These cosmetic compositions use a vehicle, or a mixture of several vehicles, present in the said compositions in concentrations of between 0.5% and 99.5% approximately, generally between 5 and 90% approximately.

Said functionalized polyorganosiloxanes of formula (I) or (I') present in the cosmetic composition forming the subject of the invention can have several functions within the said composition. Firstly, they can at least partially constitute the vehicle for the natural or synthetic active substances present in the said composition; they can thus at least partially replace the usual lipophilic vehicles. Secondly, they give the said composition specific sensory properties and can thus at least partially replace the usual emollients or conditioners, in particular the usual silicone oils. They also give cosmetic formulations transfer-resistance properties.

The said functionalized polyorganosiloxanes formula (I) or (I') are capable of replacing polyorganosiloxanes such as phenyltrimethicone, octamethyltetramethicone, etc.

The amounts of functionalized polyorganosiloxanes of formula (I) or (I') present in the cosmetic composition forming the subject of the invention depend on the desired function and the type of cosmetic formulation under consideration. A person skilled in the art is capable of determining these amounts.

Mention may be made as follows, as a guide, of the amounts by mass of functionalized polyorganosiloxanes of formula (I) or (I') which are favourably present in the cosmetic composition as a function of the desired use.

| | |
|---|---|
| Care products (creams, milks, etc.) | 0.5–5% |
| Make-up-removing products | 1–2% |
| Products for the body | 0.5–1.5% |
| Make-up products (foundations, compact powders, mascaras, eyeshadows, lipsticks, etc.) | up to 40% |
| Hygiene and cleansing products (deodorants, antiperspirants, shaving products and aqueous-alcoholic products) | 1–10% |
| Antisun products (cream, milk or oil) | up to 99%, or even more, preferably 10–40% |
| Hair products (shampoo, conditioner) | up to 5% |
| Hair care (hair beauty products) | up to 10% |

The cosmetic compositions forming the subject of the invention also contain other additives and optionally other vehicles or emollients.

Other vehicles which may be mentioned are water, alcohols such as ethanol and isopropanol, as well as other solvents such as hydrocarbons, halohydrocarbons, linalool, esters and volatile silicones. The various solvents may be miscible or immiscible with each other.

When the cosmetic compositions are in the form of sprays, tonic lotions, gels or mousses, the preferred vehicles comprise ethanol, volatile silicone derivatives or mixtures thereof.

The formulations for mousses and aerosol sprays can thus contain a propellant capable of generating the products in the form of mousses or fine uniform sprays. Examples which may be mentioned are dimethyl ether, propane, n-butane and isobutane.

Along with the vehicle, the cosmetic compositions can contain surfactants; examples which may be mentioned are anionic surfactants such as
  alkyl ester sulphonates
  alkyl sulphates
  alkylamide sulphates
  saturated or unsaturated fatty acid salts
nonionic surfactants such as
  polyoxyalkylenated alkylphenols
  glucosamides, glucamides;
  glycerolamides derived from N-alkylamines
  polyoxyalkylenated $C_8$–$C_{22}$ aliphatic alcohols
  the products resulting from the condensation of ethylene oxide with a hydrophobic compound resulting from the condensation of propylene oxide with propylene glycol,
  amine oxides
  alkylpolyglycosides and polyoxyalkylenated derivatives thereof;
  $C_8$–$C_{20}$ fatty acid amides
  ethoxylated fatty acids
  ethoxylated amides, amines and amidoamines
amphoteric and zwitterionic surfactants such as
  those of betain type, such as
    betaines
    sulpho-betaines
    amidoalkylbetaines
    and sulpho-betaines
  alkylsultaines
  the products of condensation of fatty acids and of protein hydrolysates,
  cocoamphoacetates and cocoamphodiacetates
  alkylampho-propionates or -dipropionates,
  amphoteric alkylpolyamine derivatives The other emollients can be chosen from alkylmonoglycerides, alkyldiglycerides, triglycerides such as oils extracted from plants and vegetables (palm oil, coconut oil, cotton seed oil, soybean oil, sunflower oil, olive oil, grapeseed oil, sesame oil, ground nut oil, castor oil, argan oil, etc.) or oils of marine origin (fish oils, etc.), derivatives of these oils, such as hydrogenated oils, lanolin derivatives, mineral oils or paraffinic oils, perhydrosqualane, squalene, diols such as 1,2-propanediol and 1,3-butanediol, cetyl alcohol, stearyl alcohol, oleyl alcohol, polyethylene glycols or polypropylene glycols, fatty esters such as isopropyl palmitate, 2-ethylhexyl cocoate, myristyl myristate, esters of lactic acid, stearic acid, behenic acid, isostearic acid, silicone oils combining cyclic polydimethylsiloxanes, α,ω-hydroxylated polydimethylsiloxanes, α,ωtrimethylsilyl polydimethylsiloxanes, polyorganosiloxanes such as polyalkylmethylsiloxanes, polymethylphenylsiloxanes, polydiphenylsiloxanes, aminosilicone derivatives, silicone waxes, copolyether silicones (such as the oil Mirasil DMCO sold by the company Rhône-Poulenc or DC 190 sold by Dow Corning) or mixed silicone derivatives including various types of derivatization (such as polyalkylmethylsiloxane/copolyether silicone mixed copolymers).

Other conditioners may also be present. Among these, mention may be made of those of natural or synthetic origin, such as those known under the generic CTFA name "Polyquaternium", for instance the Mirapol A15® or Mirapol 550® polymers from the company Rhône-Poulenc, cationic polysaccharide derivatives (cationic derivatives of cellulose, of guar or of carob), such as cocodimonium hydroxyethyl cellulose, guar hydroxypropyl trimonium chloride, hydroxypropyl guar hydroxypropyl trimonium chloride (Jaguar C13S®, Jaguar C162® sold by Rhône-Poulenc), volatile or non-volatile silicone derivatives, for instance amodimethicone, cyclomethicones, water-insoluble, non-volatile polyorganosiloxanes, for instance oils, resins or gums, such as diphenyldimethicone gums.

Various constituents which are useful for promoting moisturization of the skin (wetting agents) can also be added to these compositions, for instance certain carbohydrates (for example glycerol or sorbitol), polyethylene glycols or polypropylene glycols, alkoxylated derivatives of sugars or of sugar derivatives (for example methylglucose), water-soluble or water-dispersible polymers such as collagen or certain non-allergenic derivatives of marine or plant proteins (for example wheat protein hydrolysates). Thickeners, such as natural hydrocolloids (guar gum, carob gum, tara gum, etc.) or hydrocolloids derived from fermentation processes, such as xanthan gum, polysaccharides extracted from seaweed, such as carrageenans, and polycarbohydrate derivatives such as modified celluloses (for example hydroxyethylcellulose, carboxymethylcellulose), or non-ionic derivatives (for example hydroxypropylguar), anionic derivatives (carboxymethylguar) or nonionic/anionic mixed derivatives, such as carboxy-hydroxypropyl-guars or nonionic/cationic derivatives, can also be present. Mineral powders or particles such as calcium carbonate, mineral oxides in powder form or in colloidal form (particles of the order of or smaller than one micrometer in size, occasionally a few tens of nanometers), such as titanium dioxide, silica, aluminium salts generally used as antiperspirants, kaolin, talc, clays and clay derivatives, etc., and any mineral pigment used in make-up formulations, can be added to these compounds in combination.

Preserving agents such as methyl, ethyl, propyl and butyl esters of p-hydroxybenzoic acid, sodium benzoate, DMDM hydantoin or any chemical agent which prevents the proliferation of bacteria or moulds and which is among the list of authorized and/or provisionally authorized preserving agents, mentioned in Annex VI of European Directive No. 76/78/EEC, conventionally used in cosmetic compositions are generally introduced into these compositions toga proportion of from 0.01 to 3% by weight. The amount of these products is generally adjusted to avoid any proliferation of bacteria, moulds or yeasts in the cosmetic compositions.

To protect the skin or the hair against attack from the sun and UV rays, it is possible to add to these formulations sunscreens which are chemical compounds which absorb UV radiation strongly, for instance the compounds authorized in European Directive No. 76/768/EEC, its annexes and subsequent modifications of this directive, or titanium dioxide or cerium oxides in the form of powder or colloidal particles. These powders can optionally be surface-treated to increase the efficacy of their UV-stabilizing action or to facilitate their incorporation into cosmetic formulations or to inhibit the surface photoreactivity. Fragrances, dyes or pigments can be added to make the composition more pleasant for the consumer to use.

The said compositions can also con-ain resins for fixing to keratin support, in concentrations of between 0.5 and 10%, preferably between 1 and 5%. They are preferably chosen from the following resins: methyl acrylate/acrylamide copolymers, polyvinyl methyl ether/maleic anhydride copolymers, vinyl acetate/crotonic acid copolymers, octylacrylamide/methyl acrylate/butylaminoethyl methacrylate copolymers, polyvinylpyrrolidones, polyvinylpyrrolidone/methyl methacrylate copolymers, polyvinylpyrrolidone/vinyl acetate copolymers, polyvinyl alcohols, polyvinyl alcohol/crotonic acid copolymers, polyvinyl alcohol/maleic anhydride copolymers, hydroxypropylcelluloses, hydroxypropylguars, sodium polystyrenesulphonates, polyvinylpyrrolidone/ethyl methacrylate/methacrylic acid terpolymers, poly(methyl vinyl ether/maleic acid)monomethyl ethers, polyethylene glycol terephthalate/polyethylene glycol copolymers, polyethylene glycol terephthalate/polyethylene glycol/poly (sodium isophthalate sulphonate) copolymers, sulphonated polyesters containing polyorganosiloxane units; cationic resins totally or partially derived from cationic monomers such as, for example, dimethylaminoethyl methacrylate, quaternized dimethylaminoethyl methacrylate, diallyldimethyl-ammonium chloride, or mixtures thereof. These cationic resins can also be based on water-soluble natural polymers such as, for example, cationic polysaccharides, for instance cationic guar or cationic cellulose, or mixtures thereof.

The second subject of the invention consists of the use, as an emollient and/or vehicle and/or transfer-resistance agent in cosmetic compositions, of at least one of the said functionalized polyorganosiloxanes of formula (I) or (I').

Specific examples of functionalized polyorganosiloxanes of formula (I) or (I'), as well as the concentrations to be used and the nature of the various other additives, have already been mentioned above.

The functionalized polyorganosiloxanes of formula (I) or (I'), in particular the organodisiloxanes containing phenyl functions and the organotrisiloxanes containing phenylalkyl or phenylalkenyl functions of formula (III), most particularly phenylethylheptamethyltrisiloxane or mixtures (M) rich in phenylethylheptamethyltrisiloxane, give the cosmetic composition specific sensory properties.

In particular, they have, as shown by the values below, a relatively high refractive index, compared with other silicones with a high sensory signal, thus affording superior sheen properties.

| Polyorganosiloxane | $n_D$ at 25° C. |
| --- | --- |
| Mixture (M) based on phenylethylheptamethyl-trisiloxane of Example 1 | 1.4515 |
| Dimethicone V50 | 1.401 |
| 3-n-Octadecylheptamethyl-trisiloxane | 1.4330 |

The indications below give, for comparative purposes, an estimation of the set of sensory properties of the said mixture (M), compared with those of a phenyltrimethicone and of a dimethicone V50 (low viscosity).

| Sensory properties | Mixture (M) containing phenylethyl-heptamethyl-trisiloxane | Pheyltri-methicone | Dimethicone V50 |
| --- | --- | --- | --- |
| sticky | 0 | 0 | 0 |
| greasy | 0 | ++ | ++ |

| Sensory properties | Mixture (M) containing phenylethyl-heptamethyl-trisiloxane | Pheyltri-methicone | Dimethicone V50 |
|---|---|---|---|
| slippery | ++ | ++ | +++ |
| shiny | +++ | +++ | ++ |
| spreading | ++ | ++ | ++ |
| soaping | 0 | ++ | 0 |
| residual film | | | |
| dry | +++ | 0 | 0 |
| homogeneity | +++ | +++ | +++ |

"O" means "non": non-sticky, non-greasy, non-soapy, etc. depending on the parameter considered.
"+++" means "very": very slippery, very greasy, very homogeneous, very shiny, very dry, depending on the parameter considered.

The use of the functionalized polyorganosiloxanes of formula (I) and (I'), in particular the organodisiloxanes containing phenyl functions and the organotrisiloxanes containing phenylalkyl or phenylalkenyl functions of formula (III), gives the skin a silky feel and reduces the greasy and sticky feel which may be obtained from the other emollients introduced into the cosmetic formulation.

For hair use, the said functionalized polyorganosiloxanes of formula (I) or (I'), in particular the organodisiloxanes containing phenyl functions and the organotrisiloxanes containing phenylalkyl or phenylalkenyl functions of formula (III), are conditioners that provide sheen, disentangling, volume and ease of styling properties and improve the appearance of the hair. For antisun use, these functionalized polyorganosiloxanes are good agents for dissolving sunscreens. Thus, phenylethylheptamethyltrisiloxane or the mixture (M) can dissolve more than 200% of its weight of octyl methoxycinnamate (Parsol MCX from Givaudan).

A third subject of the invention consists of a process for giving cosmetic compositions sensory and transfer-resistance properties, or for improving the sensory and transfer-resistance properties of cosmetic compositions, by addition of at least one of the functionalized polyorganosiloxanes of formula ((I) or (I') to the said cosmetic compositions.

The present invention is also directed towards a process for conveying lipophilic active materials in cosmetic compositions, by dissolving the said active materials in at least one of the functionalized polyorganosiloxanes of formula (I) or (I').

The preferred functionalized organotrisiloxanes of formula (I) or (I') and the amounts of the said polyorganosiloxanes used, as well as of the other solvents or additives which may be present, have already been mentioned above.

The examples which follow are given as a guide.

EXAMPLE 1

Hydrosilylation of Styrene with Heptamethyltrisiloxane 1803 g (11.12 mol) of hexamethyldisiloxane (HMDS) and 4.15 g of a Karstedt platinum solution with a titre of 11.5% platinum (0) are introduced with the aid of a pump into a 10-liter reactor. The reaction mass is brought to 90° C. and 4150 g (19.3 mol) of heptamethyltrisiloxane (MD'M) and 2207 g (21.22 mol) of styrene are added simultaneously.

Monitoring of the predominant species by gas chromatography shows that the reaction is virtually quantitative (in % by weight).

| Time | HMDS | Styrene | MD'M | X-HMTS | Y-HMTS | Z-HMTS |
|---|---|---|---|---|---|---|
| 1 h | 54.9 | 0.6 | 1.5 | 30.4 | 0.8 | 5.6 |
| 2 h | 36.9 | 2.0 | 1.6 | 42.9 | 1.7 | 7.8 |
| 3 h | 30.3 | 2.3 | 2.1 | 47.7 | 2.5 | 8.3 |
| 4 h | 24.2 | 2.1 | 2.8 | 53.2 | 3.2 | 9.3 |
| 5 h | 21.7 | 3.2 | 2.5 | 53.2 | 3.3 | 9.3 |

The content of free styrene in the reaction mass, at the end of the reaction, represents 88% of the excess styrene used, which is proof of a very poor polymerization. The remainder to 100% consists of the product of reaction of the MD'M side products (in particular MD'DM and MM') with styrene.

In this table,

X-HMTS has the following meaning $Me_3Si$—O—$Si(Me)$(X)—O—$SiMe_3$, in which X represents the —$CH_2$—$CH_2$—Ph function Y-HMTS has the following meaning $Me_3Si$—O—$Si(Me)$(Y)—O—$SiMe_3$, in which Y represents the —CH=CH—Ph function Z-HMTS has the following meaning $Me_3Si$—O—$Si(Me)$(Z)O—$SiMe_3$, in which Z represents the —$CH(CH_3)$—Ph function with Me representing methyl and Ph representing phenyl.

Distillation

The reaction mass is then concentrated (evaporation of the volatiles at 110° C. under 20 mbar for 7 hours). 5827 g of a coloured product with the following composition are collected (values in % by weight):

| HMDS | Styrene | MD'M | X-HMTS | Y-HMTS | Z-HMTS |
|---|---|---|---|---|---|
| 0.13 | 0.13 | 0.12 | 77.8 | 4.9 | 14.6 |

Hydrogenation 700 g of this coloured product are placed in a 1 liter autoclave reactor. 14 g (i.e. 2% by weight) of a platinum catalyst on charcoal with a Pt titre of 2% are introduced. The reaction mass is brought to 100° C. under a pressure of 20 bar of hydrogen. After reaction for three hours with stirring, the reaction mass is cooled and returned to atmospheric pressure. After filtration, 692 g of a colourless product with the composition below are obtained:

| HMDS | Styrene | MD'M | X-HMTS | Y-HMTS | Z-HMTS |
|---|---|---|---|---|---|
| 0.13 | 0 | 0.1 | 80.75 | 1.10 | 14.3 |

After distillation on a column packed with Rashig rings (height=40 cm), 563.3 g (yield=81.4%) of a mixture (M) with the following composition are collected:

| HMDS | Styrene | MD'M | X-HMTS | Y-HMTS | Z-HMTS |
|---|---|---|---|---|---|
| 0 | 0 | 0 | 81.5 | 1.04 | 16.6 |

EXAMPLE 2

| Deodorant in the form of a transparent stick | | |
|---|---|---|
| (1) | Mixture (M) based on phenylethylheptamethyltrisiloxane | 9% |
| (2) | polypropoxylated myristyl ester of propionic acid | 70% |
| (3) | propylene glycol | 14% |
| (4) | triclosan | 0.3% |
| (5) | sodium stearate | 6% |
| (6) | fragrance | qs |

This composition is obtained by preparing a premix of (1), (2) and (3) at about 60° C., in which (4) and (5) are dissolved. The mixture is left to cool and the fragrance is added.

EXAMPLE 3

| Dry antisun oil | |
|---|---|
| Mixture (M) based on phenylethylheptamethyltrisiloxane | 27% |
| isopropyl palmitate | 25% |
| diisopropyl adipate | 25% |
| Mirasil C-DPDM | 20% |
| octyl methoxycinnamate | 3% |

This composition is obtained by simple mixing of its constituents.

EXAMPLE 4

| Hair lotion for treating the tips of the hair | |
|---|---|
| Mixture (M) based on phenylethyl heptamethyl-trisiloxane | 5% |
| Mirasil C-DPDM | 90% |
| ethanol | 5% |

This composition is obtained by simple mixing of its constituents.

EXAMPLE 5

| Transfer-resistant lipstick | | |
|---|---|---|
| (1) | Mixture (M) based on phenylethylheptamethyltrisiloxane | 35% |
| (2) | pentacyclomethicone | 25% |
| (3) | ozokerite | 5% |
| (4) | polyisobutene | 5% |
| (5) | microcrystalline wax | 15% |
| (6) | pigments and titanium oxide qs | 100% |

The mixture of (3), (4) and (5) is melted at about 60° C.

A mixture of (1), (5) and (6) is prepared at about 60° C.

The two preparations are mixed together and (2) is added.

EXAMPLE 6

| Transfer-resistant foundation | |
|---|---|
| (1) Mixture (M) based on phenylethylheptamethyltrisiloxane | 20% |
| (2) pentacyclomethicone | 50% |
| (3) pigments and titanium oxide | 20% |
| (4) Parsol MCX from Givaudan | 3% |
| (5) bentone gel | 3% |

(4) is dissolved in a mixture of (1) and (2).
(3) and (5) are then introduced.

What is claimed is:

1. A cosmetic composition, comprising:

more than 75% by mass of functionalized polyorganosiloxane of formula (a):

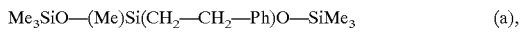

$$Me_3SiO—(Me)Si(CH_2—CH_2—Ph)O—SiMe_3 \qquad (a),$$

from 10 to 20% by mass of functionalized polyorganosiloxane of formula (b):

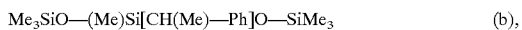

$$Me_3SiO—(Me)Si[CH(Me)—Ph]O—SiMe_3 \qquad (b),$$

from 0 to 2% by mass, of fimctionalized polyorganosiloxane of formula (c):

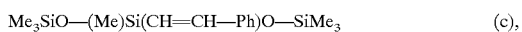

$$Me_3SiO—(Me)Si(CH=CH—Ph)O—SiMe_3 \qquad (c),$$

optionally, a functionalized polyorganosiloxane of formula (d):

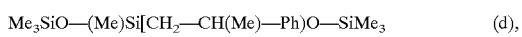

$$Me_3SiO—(Me)Si[CH_2—CH(Me)—Ph]O—SiMe_3 \qquad (d),$$

optionally, a fimctionalized polyorganosiloxane of formula (e):

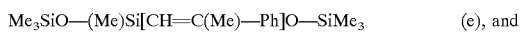

$$Me_3SiO—(Me)Si[CH=C(Me)—Ph]O—SiMe_3 \qquad (e), and$$

optionally, a linear functionalized polyorganosiloxane of formula (f) below:

$$PhSi(Me)_2—O—Si(Me)_2Ph \qquad (f),$$

wherein Me is a methyl group and Ph is a phenyl group.

* * * * *